US006232443B1

(12) United States Patent
Getzenberg

(10) Patent No.: US 6,232,443 B1
(45) Date of Patent: May 15, 2001

(54) RENAL NUCLEAR MATRIX PROTEINS, POLYNUCLEOTIDE SEQUENCES ENCODING THEM, AND THEIR USE

(75) Inventor: Robert H. Getzenberg, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/050,991

(22) Filed: Mar. 31, 1998

Related U.S. Application Data

(60) Provisional application No. 60/041,860, filed on Apr. 8, 1997.

(51) Int. Cl.[7] .......................... A61K 39/00; G01N 33/48; G01N 33/53; G01N 33/574; C07K 16/00
(52) U.S. Cl. .......................... 530/358; 435/7.1; 435/7.23; 435/64; 436/813; 530/387.1; 530/388.1; 530/350; 424/277.1
(58) Field of Search .................................. 435/7.23, 7.1; 436/64, 813; 530/387.1, 388.1; 424/277.1

(56) References Cited

U.S. PATENT DOCUMENTS

| | | | |
|---|---|---|---|
| 4,882,268 | 11/1989 | Penman et al. | 435/5 |
| 4,885,236 | 12/1989 | Penman et al. | 435/6 |
| 5,273,877 | 12/1993 | Fey et al. | 435/6 |
| 5,547,928 | 8/1996 | Wu et al. | 514/2 |
| 5,824,490 | 10/1998 | Coffey et al. | 435/7.23 |
| 5,849,509 | 12/1998 | Coffey et al. | 435/7.23 |
| 5,866,535 | 2/1999 | Getzenberg et al. | 514/2 |

FOREIGN PATENT DOCUMENTS

| | | |
|---|---|---|
| WO87/03910 | 7/1987 | (WO) . |
| WO93/09437 | 5/1993 | (WO) . |
| WO94/00573 | 1/1994 | (WO) . |
| WO94/18222 | 8/1994 | (WO) . |
| WO95/16919 | 6/1995 | (WO) . |
| WO97/16206 | 9/1997 | (WO) . |

OTHER PUBLICATIONS

Miyanaga, N., et al., "Nuclear Matrix Proteins as a Urine Marker for Transitional Cell Carcinoma of the Bladder". The Journal of Urology Supplement, vol. 153, No. 4 (XP–002068914) Apr. 23, 1995, p. 457A.

Merrifield, S., et al., "The Performance of the NMP22™ Test Kit: A Quantitative Enzyme Immuno–Assay for Bladder Cancer", *Tumor Biology*, 17 (suppl 1) (1996). (XP–002068915), p. 19.

Getzenberg, R., et al., "Bladder Cancer–associated Nuclear Matrix Proteins", *Cancer Research* vol. 56, No. 7, pp. 1690–1694, (1996). (XP002068894).

Konety, B.R., et al., "Identification of Nuclear Matrix Protein Alterations Associated with Renal Cell Carcinoma", *The Journal of Urology*, vol. 159, No. 4, pp. 1359–1363 (1998). (XP002068895).

Eberharter A., et al., "Nuclear Matrix of the lower eukaryote *Physarum polycephalum* and the mammalian epithelial LLC–PK$_1$ cell line—A comprehensive investigation of different preparation procedures", vol. 212, No. 2 pp. 573–580 (1992). (XP02068893).

Keesee, S.K., et al., "Utilization of Nuclear Matrix Proteins for Cancer Diagnosis", *Critical Reviews in Eukaryotic Gene Expression*, vol. 6, No. 2&3, pp. 189–214 (1996). (XP002069158).

Getzenberg, R. H., "Nuclear Matrix and the Regulation of Gene Expression: Tissue Specificity", *Journal of Cellular Biochemistry*, vol. 55, pp. 22–31 (1994).

Getzenberg, R.H., et al., "Identification of Nuclear Matrix Proteins in the Cancer and Normal Rat Prostate", *Cancer Research*, vol. 51, pp. 6514–6520 (1991).

Berezney, R., et al., "Identification of a Nuclear Protein Matrix", *Biochemical and Biophysical Research Communications*, vol. 60, No. 4 (1974). p. 1410–1417.

Fey, E.G., et al., "The Nuclear Matrix: Defining Structural and Functional Roles", *Eukaryotic Gene Expression*, pp. 127–143 (1991).

Fey, E.G., et al., "Tumor promoters induce a specific morphological signature in the nuclear matrix–intermediate filament scaffold of Madin–Darby canine kidney (MDCK) cell colonies", *Proc. Natl. Acad. Sci. USA*, vol. 81, pp. 4409–4413 (1984).

Fey, E.G., et al., "Nuclear matrix proteins reflect cell type of origin in cultured human cells", *Proc. Natl. Acad. Sci. USA*, vol. 85, pp. 121–125 (1988).

Fey, E.G., et al., "Epithelial Cytoskeletal Framework and Nuclear Matrix–Intermediate Filament Scaffold: Three–dimensional Organization and Protein Composition", *The Journal of Cell Biology*, vol. 98, pp. 1973–1984 (1984).

Weidner, N., et al., "Rapid Communication, Localization of Nuclear Matrix Proteins (NMPs) in Multiple Tissue Types with NM–200.4™ (An Antibody Strongly Reactive with NMPs Found in Breast Carcinoma)", *American Journal of Pathology*, vol. 138, No. 6, pp. 1293–1298 (1991).

Huse, W.D., et al., "Generation of a Large Combinatorial Library of the Immunoglobulin Repertoire in Phage Lambda", *Research Article*, pp. 1275–1281 (1989).

Mullinax, R.L., et al., "Identification of human antibody fragment clones specific for tetanus toxoid in a bacteriophage λ immunoexpression library", *Proc. Natl. Acad. Sci. USA*, vol. 87, pp. 8095–8099 (1990).

Diener, E., et al., "Specific Immunosuppression by Immunotoxins Containing Daunomycin", *Science*, vol. 231, pp. 148–150 (1986).

(List continued on next page.)

Primary Examiner—Robert A. Schwartzman
Assistant Examiner—Janet Epps
(74) Attorney, Agent, or Firm—Foley & Lardner

(57) ABSTRACT

Nuclear matrix proteins (NMP) are useful markers in diagnosing and monitoring the stage of malignancy of a cell, and in treating cell proliferative disorders associated with the NMP.

14 Claims, No Drawings

OTHER PUBLICATIONS

Greiner, J.W., "Recombinant Interferon Enhances Monoclonal Antibody—Targeting of Carcinoma Lesions in Vivo", pp. 895–898 (1987). Science vol. 235, Iss. 4791.

Wolff, B., et al., "The Use of Monoclonal Anti–Thy$_1$IgG$_1$ for the Targeting of Liposomes to AKR–A Cells In Vitro and In Vivo", *Biochimica et Biophysica Acta,* vol. 802, pp. 259–273 (1984).

Weintraub, H.M., "Antisense RNA and DNA", *Scientific American,* pp. 40–46 (1990). Jan.

Cech, T.R., PhD., "Ribozymes and Their Medical Implications", *JAMA,* vol. 260, No. 20, pp. 3030–3034 (1988).

Haseloff, J., et al., "Simple RNA enzymes with new and highly specific endoribonuclease activities", *Nature,* vol. 334, pp. 585–591 (1988).

Bejany, D.E., et al., Malignant Vesical Tumors Following Spinal Cord Injury, *The Journal of Urology,* vol. 138, pp. 1390–1392 (1987).

Kaufman, J.M., et al., "Bladder Cancer and Squamous Metaplasia in Spinal Cord Injury Patients", pp. 967–971 (1977). Journal of Urology vol. 118, No. 6.

Melzak, J., M.D., "The Incidence of Bladder Cancer in Paraplegia", *Paraplegia,* pp. 85–96. (Aug. 1996) vol. 4.

Nyquist, R.H., M.D., et al., "Mortality and Survival in Traumatic Myelof During Nineteen Years, from 1946 to 1965", *Paraplegia,* pp. 22–48. (May 1967) vol. 5(1).

El–Masri, W.S., "Bladder Cancer After Spinal Cord Injury", *International Medical Society of Paraplegia,* pp. 265–270 (1981). vol. 19, No. 5.

Geisler, W.O., et al., "Survival In Traumatic Transverse Myelitis", *Paraplegia,* vol. 14, pp. 262–275 (1977).

Hackler, R.H., "A 25–Year Prospective Mortality Study In The Spinal Cord Injured Patient: Comparison With The Long–Term Living Paraplegic", *The Journal of Urology,* vol. 117, pp. 486–488 (1977).

Pound, C.R., et al., "Differential Nuclear Matrix Protein (NMP) Patterns In Normal Renal Tissue And Renal Cell Carcinoma (RCC)". 92$^{nd}$ Annual Meeting of the American Urological Association, New Orleans, LA, USA (1997) J. of Urol., vol. 157 (4 suppl.) (1997) (XP–002076374) p. 279.

Konety, B.R., et al., "Characteristic Nuclear Matrix Protein Alterations In Renal Cell Carcinoma (RCC)".). 92$^{nd}$ Annual Meeting of the American Urological Association, New Orleans, LA, USA (1997) J. of Urol., vol. 157 (4 suppl.) (1997) (XP–002076375) p. 276.

Gordon, J.N., et al., "Altered Extracellular Matrices Influence Cellular Processes and Nuclear Matrix Organizations of Overlying Human Bladder Urothelial Cells", Cancer Research, vol. 53, pp. 4971–4977 (1993).

Cupo, J., "Electrophoretic analysis of nuclear matrix proteins and the potential clinical applications", *Elsevier Science Publishers B.V.,* pp. 389–406 (1991).

Partin, A.W., et al., "Nuclear Matrix Protein Patterns in Human Benign Prostatic Hyperplasia and Prostate Cancer", *Cancer Research,* vol. 53, pp. 744–746 (1993).

Russell, P.J. et al., "Preclinical studies of monoclonal antibodies for intravesical radioimmunotherapy of human bladder cancer," Cell biophysics, vols. 24/25, pp. 155–161 (1994).

Kingsley E.A. et al., "Characterisation of the anti–bladder–cancer monoclonal antibody BLCA –8: identification of its antigen as a neutral glycolipid," Cancer Immunology, Immunotherapy, vol. 41, No. 6, pp. 348–354 1995) (XP000872998).

Fradet Y., "Molecular and immunologic approaches in the management of bladder cancer," Urologic Clinics of North America, vol. 18, No. 3, pp. 515–524 (1991) (XP000881253).

Replogle–Schwab R. et al., "The utilization of nuclear matrix proteins for cancer diagnosis," Critical Reviews in Eukaryotic Gene Expression, vol. 6, Nos. 2–3, pp. 103–113 (1996) (XP000881255).

Pirtskalaishvili G. et al., "Use of urine–based markers for detection and monitoring of bladder cancer," Techniques in Urology, vol. 5, No. 4, pp. 179–184 (1999) (XP000881344).

J.E. Celis et al., "Expression of the transformation–sensitive protein "cyclin" in normal human epidermal basal cells and simian virus 40–transformed keratinocytes," Proc. Natl Acad. Sci. USA, vol. 81, pp. 3128–3132 (1984).

J.E. Celis et al., "Intermediate filaments in monkey kidney TC7 cells: Focal centers and interrelationship with other cytoskeletal systems," Proc. Natl Acad. Sci. USA, vol. 81, pp. 1117–1121 (1984).

R. G. DiScipio et al., "Nucleotide sequence of cDNA and derived amino acid sequence of human complement component C9," Proc. Natl Acad. Sci. USA, vol. 81, pp. 7298–7302 (1984).

R.B. Merrifield, "Solid Phase Peptide Synthesis. I. The synthesis of a Tetrapeptide," J. Am. Chem. Soc., vol. 85, No. 14, pp. 2149–2154 (1963).

Stewart and Young, "Solid Phase Peptide Synthesis," Freeman Publ. 1969, pp. 27–61.

J.Y. Douillard et al., "Monoclonal Antibodies Specific Immunotherapy of Gastrointestinal Tumors," Hybridoma, vol. 5, Suppl. 1 (1986) pp. S139–S149.

Matritech, NMP22® Test Kit (Jun. 1996) pp. 1–39.

R. Fraley et al., "New Generation liposomes: the engineering of an efficient vehicle for intracellular delivery of nucleic acids," Trends Biochem. Sci., vol. 6, pp. 77–80 (1981).

RENAL NUCLEAR MATRIX PROTEINS, POLYNUCLEOTIDE SEQUENCES ENCODING THEM, AND THEIR USE

This application claims benefit under 35 USC 119(e) of provisional application No. 60/041,860, filed Apr. 8, 1997.

This invention was made with support from the National Kidney Fund of Western Pennsylvania and from the National Kidney Cancer Association.

BACKGROUND OF THE INVENTION

The present invention relates generally to renal nuclear matrix proteins, called "NMPs" here, and more specifically to novel nuclear matrix proteins of the kidney which are associated with cell-proliferative disorders.

U.S. Pat. Nos. 4,882,268 and 4,885,236, both issued to Fey and Penman, disclose certain NMPs and discuss their possible uses in identifying the origin of a tissue sample. In addition to identifying the origin of a tissue sample, the patents also discuss possible uses of NMPs to indicate certain disease states of a cell, such as viral infection, cancer, chromosomal defects or autoimmune disease. Specific NMPs discussed in the patents include those from human colon, lung, adrenal cortex and bladder cell lines.

The early diagnosis of renal cancer is central to the effective treatment of the disease. Currently, there are no methods available to easily and specifically identify the presence of renal cancer cells based on NMPs.

The nuclear matrix is the structural component of the nucleus that determines nuclear morphology, organizes the DNA in a three-dimensional fashion that is tissue specific, and has a central role in the regulation of a number of nuclear processes including the regulation of gene expression. The nuclear matrix has been demonstrated to play a central role in the regulation of important cellular processes such as DNA replication and transcription. Getzenberg, *J. Cell Biochem.* 55: 22–31 (1994). The nuclear matrix is the framework or scaffolding of the nucleus and consists of the peripheral laminas and pore complexes, an internal ribonucleic protein network, and residual nucleoli. Berezney et al., *Biochem. Biophys. Res. Comm.* 60: 1410–17 (1974). The nuclear matrix consists of approximately 10% of the nuclear proteins and is virtually devoid of lipids, DNA and histones. Fey et al., *Crit. Rev. Eukaryotic Gene Expression* 1: 127–44 (1991).

A majority of the known NMPs are common to all cell types and physiologic states. A number of laboratories have identified NMPs which may be unique to certain cell types or states. Mitogenic stimulation and the induction of differentiation have been demonstrated to alter the composition of nuclear matrix proteins and structure. The nuclear matrix contains a number of associated proteins that have been demonstrated to be involved in transformation. Berezney first showed that the nuclear matrix is altered in transformation, examining hepatoma nuclear matrix proteins. Berezney et al., *Cancer Res.* 39: 3031–39 (1979). Fey and Penman demonstrated that tumor promoters induce a specific morphologic signature in the nuclear matrix-intermediate filament scaffold of kidney cells. Fey et al., *Proc. Nat'l Acad. Sci. USA* 81: 859–66 (1984). Fey and Penman went on to demonstrate that the pattern of NMPs differed between normal and tumorigenic cell lines. Fey et al., loc. cit. 85: 121–25 (1989). An antibody to a nuclear matrix protein, termed NM-200.4, was raised from the breast carcinoma cell line T-47D. Weidner et al., *Am. J. Path.* 138: 1293–98 (1991). This antibody reacts strongly with human breast carcinoma specimens as well as specimens from lung, thyroid, and ovarian cancers, but does not react with normal epithelial cells of similar origin, raising the possibility of the use of certain anti-NMP antibodies as diagnostic tools.

Exposure of canine kidney cells to various tumor promoters has also been found to alter the nuclear matrix-intermediate filament organization in these epithelial cells. Fey et al., *Proc. Nat'l Acad. Sci. USA* 81: 4409–4413 (1984).

It has been demonstrated with the Dunning rat model of prostate cancer that nuclear matrix protein composition is altered when comparing the normal dorsal prostate with the spontaneously arisen rat prostate adenocarcinomas. In U.S. Pat. No. 5,849,509, the entire contents of which are incorporated by reference herein, when human prostate samples were examined, nuclear matrix proteins were identified that (1) were present only in the normal prostate and were missing in both prostate cancer and benign prostatic hyperplasia (BPH) (normal pattern), (2) were found only in the prostate cancer cells and missing in the normal prostate and BPH (prostate cancer pattern), and (3) were found in both normal and BPH samples but were absent from prostate cancers.

In co-pending U.S. application Ser. No. 08/742,850 (now U.S. Pat. No. 5,866,535), the entire contents of which are incorporated by reference herein, NMPs are disclosed which are present only in normal bladder cells and are absent in bladder cancer cells. Also, the application discloses other NMPs that are found only in bladder cancer cells but are absent in normal bladder cells.

No nuclear matrix proteins have been isolated heretofore, however, that are linked specifically to renal cancer.

SUMMARY OF THE INVENTION

The present invention relates to nuclear matrix proteins that are able to differentiate cancerous renal cells from normal renal cells, polynucleotide sequences encoding them, and their methods of use. Five proteins, respectively designated RCCA-1, RCCA-2, RCCA-3, RCCA-4, and RCCA-5, have been discovered that are present in all cancerous renal cells that are not present in the normal renal cells, and one protein (referred to as RCNL-1) has been discovered that is unique to normal renal tissue. These proteins are useful for diagnosing and producing treatments for cell proliferative disorders of the kidney.

DETAILED DESCRIPTION OF PREFERRED EMBODIMENTS

According to one aspect, the present invention is directed to a purified nuclear matrix protein or a fragment thereof, which is present in normal renal cells but absent in cancerous renal cells, or which is absent in normal renal cells but present in cancerous renal cells. In particular, the present invention relates to a protein that is present in normal renal cells but absent in cancerous renal cells, which is RCNL-1. In addition, the present invention relates to a protein that is absent in normal renal cells but present in cancerous renal cells selected from the group consisting of RCCA-1, RCCA-2, RCCA-3, RCCA-4, and RCCA-5.

Another embodiment of the present invention is a purified polynucleotide sequence encoding the above identified NMPs or NMP fragments of the preceding embodiment. Another embodiment is a purified polynucleotide sequence which hybridizes to the polynucleotide sequence encoding the above-mentioned NMPs or NMP fragments.

Another embodiment is a host cell transformed with a polynucleotide sequence encoding the above-mentioned NMPs or NMP fragments. Transformation of a host cell with recombinant DNA may be carried out by conventional techniques known in the art. Where the host is prokaryotic, such as *E. coli,* competent cells which are capable of DNA uptake can be prepared from cells harvested after the exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as micro-injection, electroporation, insertion of a plasmid encased in liposomes, or virus vectors may be used. Eukaryotic cells can also be cotransformed with DNA sequences encoding the NMPs of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. EUKARYOTIC VIRAL VECTORS, Gluzman (ed.), Cold Spring Harbor Laboratory, 1982.

Isolation and purification of the NMPs or NMP fragments expressed by a transformed host may be carried out by conventional means including preparative chromatography and immunological separations involving monoclonal or polyclonal antibodies. Antibodies provided in the present invention are immunoreactive with NMP polypeptide or fragments thereof.

Another embodiment of the invention comprehends a recombinant expression vector containing the above-mentioned polynucleotide sequences. Preferably, the vector is a virus. Preferred viruses are RNA viruses and preferred RNA viruses are retroviruses. Another preferred vector is a liposome, preferably a target-specific liposome which may be targeted with, for example, an antibody or ligand. Another preferred vector is a plasmid.

A further embodiment of the invention is an antibody which binds to the above-mentioned NMPs or NMP fragments. The antibody may be polyclonal or monoclonal.

Yet another embodiment is a method for detecting a cell proliferative disorder in a subject, comprising contacting a cellular component from the subject with an antibody or nucleic acid probe which binds to a cellular component associated with the cell proliferative disorder. Preferably, the cellular component is taken from the subject's kidney and is preferably nucleic acid. Preferably, the nucleic acid is DNA encoding the above-mentioned NMPs or NMP fragments. Also preferred as a nucleic acid is RNA. Another preferred cellular component is the above-mentioned NMPs or NMP fragments.

Preferably, the nucleic acid probe specifically hybridizes to the above-mentioned cellular component. When the reagent is a nucleic acid probe, it is preferably detectably labeled. Preferred labels include a radioisotope, a bioluminescent compound, a chemiluminescent compound, a fluorescent compound, a metal chelate, and an enzyme.

Alternatively, if the cellular component is an NMP or NMP fragment, then an antibody is used which specifically binds to the NMP or NMP fragment. As noted above, the antibody may be monoclonal or polyclonal.

Another embodiment is a method of treating a cell proliferative disorder associated with a protein selected from the group consisting of RCCA-1, RCCA-2, RCCA-3, RCCA-4, RCCA-5, and RCNL-1, comprising administering to a subject with the disorder a therapeutically effective amount of an antisense polynucleotide sequence that blocks the sequences encoding the above-mentioned NMPs. In this embodiment, the treatment is designed to block the expression of one or more NMPs which give rise to the cell proliferative disorder.

In an alternative method of treatment, instead of using an antisense polynucleotide sequence, a polynucleotide sequence is used which encodes one of the above-mentioned NMPs. In this embodiment, the treatment is designed to provide the subject with one or more NMPs that prevent or ameliorate the cell proliferative disorder.

In another method of treatment, an antibody is administered to the subject which is capable of blocking the function of one or more of the above NMPs.

Another embodiment is a method of gene therapy, comprising introducing into the cells of a host subject an expression vector comprising a polynucleotide sequence encoding one or more of the above-mentioned NMPs. Preferably, the expression vector is introduced into the cells of the host subject ex vivo, yielding transformed cells, and the transformed cells then are reintroduced into the subject. A preferred expression vector for this purpose is an RNA virus, preferably a retrovirus.

The present invention also relates to a method for identifying a composition which blocks or enhances the function of a renal cell NMP. This embodiment comprises:

(a) incubating NMP-containing renal cells with a test composition under conditions that allow the renal cells and test composition to interact, and then (b) measuring whether the test composition blocks or enhances the function of the renal cell NMP.

Still another embodiment is a kit for detecting a cell-proliferative disorder of the kidney comprising a nucleic acid probe that binds to a polynucleotide sequence encoding one of the above-mentioned NMPs. Preferably, the probe is labeled for ease of detection with a label as described above. Alternatively, the kit may comprise an antibody which specifically binds to one of the above-mentioned NMPs. Still another alternative is to use an oligonucleotide primer in the kit that permits amplification of a target polynucleotide sequence encoding one of the above-mentioned NMPs, for example, by polymerase chain reaction (PCR) amplification. Preferably, the kit further includes printed instructions for using the probe or antibody and/or other reagents contained in the kit. Suitable carriers can be provided in the kits which maintain the probes and/or antibodies in active form prior to use.

The NMPs of the present invention include fragments and conservatively substituted variants thereof. Minor modifications of the NMP primary amino acid sequence may result in proteins which have substantially equivalent activity as compared to the NMP polypeptide described herein. Such modifications may be deliberate, as by site-directed mutagenesis, or may be spontaneous. Such modifications include deletion of non-essential amino acids. All of the polypeptides produced by these modifications are included herein as long as the biological activity of the native NMP still exists. Further, deletion of one or more amino acids can also result in a modification of the structure of the resultant molecule without significantly altering its biological activity. This can lead to the development of a smaller active molecule which would have broader utility.

The term "conservative substitution" as used herein denotes the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

Peptides of the invention can be synthesized by the well known solid phase peptide synthesis methods described, for example, by Merrifield, *J. Am. Chem. Soc.* 85: 2149 (1962), and by Stewart and Young, SOLID PHASE PEPTIDES SYNTHESIS 27–62 (Freeman Publ., 1969).

The polyclonal and monoclonal antibodies of the invention are immunoreactive with the NMPs or immunogenic fragments of the NMPs. If desired, polyclonal antibodies can be further purified, for example, by binding to and elution from a matrix to which NMP polypeptide is bound or by utilizing common nuclear matrix proteins to selectively remove non-specific antibodies. Antibody which consists essentially of pooled monoclonal antibodies with different epitopic specificities, as well as distinct monoclonal antibody preparations are provided. The term "antibody" as used in this invention includes intact molecules as well as fragments thereof, such as Fab and F(ab')$_2$ fragments, which are functionally capable of binding an epitopic determinant of an NMP.

A preferred method for the identification and isolation of antibody binding domains which exhibit binding with NMP is the bacteriophage λ vector system. This vector system has been used to express a combinatorial library of Fab fragments from the mouse antibody repertoire in *Escherichia coli*, see Huse et al., *Science* 246: 1275–81 (1989), and from the human antibody repertoire. Mullinax et al., *Proc. Nat'l Acad. Sci. USA* 87: 8095–99 (1990).

The phrase "cell-proliferative disorder" here denotes malignant as well as non-malignant (or benign) disorders of the kidney. This phrase further encompasses hyperplastic disorders of the kidney. The cells comprising these proliferative disorders often appear morphologically and genotypically to differ from the surrounding normal tissue. As noted above, cell-proliferative disorders may be associated, for example, with expression or absence of expression of the NMPs of the invention. Expression of an NMP at an inappropriate time during the cell cycle or in an incorrect cell type may result in a cell-proliferative disorder. The NMP-encoding polynucleotide in the form of an antisense polynucleotide is useful in treating hyperplasia and malignancies of the kidney. When the cell-proliferative disorder is associated with NMP expression, (e.g., RCCA-1, 2, 3, 4 and/or 5), an antisense NMP polynucleotide sequence or NMP binding antibody can be introduced into the renal cells to block the expression and/or function of the NMP. Alternatively, when the cell proliferative disorder is associated with under-expression or expression of a mutant NMP polypeptide (e.g., RCNL 1), a polynucleotide sequence encoding the missing or under-expressed NMP can be introduced into the cell.

For purposes of the invention, an antibody or nucleic acid probe specific for an NMP may be used to detect the presence of the NMP polypeptide (in the case of an antibody probe) or polynucleotide (in the case of the nucleic acid probe) in biological fluids or tissues suspected of containing the NMP. Oligonucleotide primers based on any coding sequence region in the NMP sequence are useful for amplifying DNA or RNA, for example by PCR. Any specimen containing a detectable amount of antigen can be used. A preferred sample of this invention is tissue taken from the kidney. Alternatively, biological fluids which may contain cells of the kidney may be used.

The term "subject" as used in this description to denote mammals, preferably humans.

Another technique which may also result in greater sensitivity consists of coupling the probe to low molecular weight haptens. These haptens can then be specifically detected by means of a second reaction. For example, it is common to use such haptens as biotin, which reacts with avidin, or dinitrophenol, pyridoxal, and fluorescein, which can react with specific antihapten antibodies.

The method for detecting a cell expressing a particular NMP of the invention or a cell-proliferative disorder associated with an NMP, described above, can be utilized for detection of residual kidney cancer or other malignancies or benign hyperplasia conditions in a subject in a state of clinical remission. Additionally, the method for detecting an NMP polypeptide in cells is useful for detecting a cell-proliferative disorder by identifying cells expressing specific NMPs in comparison with NMPs expressed in normal cells. Using the method of the invention, NMP expression can be identified in a cell and the appropriate course of treatment can be employed (e.g., NMP-encoding or antisense gene therapy, as well as conventional chemotherapy). Since the expression pattern of the NMPs of the invention vary with the stage of malignancy of a cell, a sample of renal tissue can be screened with a panel of NMP-specific reagents (e.g., nucleic acid probes or antibodies to NMPs) to detect NMP expression and diagnose the stage of malignancy of the cell.

The monoclonal antibodies of the present invention are suitable for use in immunoassays in which they can be utilized in liquid phase or bound to a solid-phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be performed utilizing immunoassays which are run in either the forward, reverse, or simultaneous modes, including immunohistochemical assays on physiological samples. Alternatively, the antibody of the invention can be used to detect NMPs present in electrophoretically dispersed gel protocols such as Western blots and two-dimensional gels.

The monoclonal antibodies of the invention can be bound to many different carriers and used to detect the presence of NMP. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-NMP immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers." The "blockers" are used at a level high enough to maintain the proper sensitivity yet inhibit any unwanted interference by mutually occurring cross reactive proteins in the specimen (normally 1–100 µg/µl).

In this description, the term "epitope" denotes any determinant capable of specific interaction with the monoclonal antibodies of the invention. Epitopic determinants usually comprise chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of delectably labeled monoclonal antibody is administered in sufficient quantity to enable detection of the site having the NMP antigen for which the monoclonal antibody is specific. The dosage of detectably labeled monoclonal antibody for in vivo diagnosis will vary depending on such factors as age, sex, and extent of disease of the individual. The dosage of monoclonal antibody can vary from about 0.001 mg/m$^2$, to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of an NMP-associated cell-proliferative disorder. Thus, by measuring the increase or decrease in the number of cells expressing a NMP or changes in NMP present in various body fluids, such as ejaculate or urine, it would be possible to determine whether a particular therapeutic regimen aimed at ameliorating the disorder is effective.

The monoclonal antibodies of the invention can also be used, alone or in combination with effector cells, see Douillard et al., *Hybridoma* 5 (Supp. 1): S139 (1986), for immunotherapy in an animal having a cell proliferative disorder which expresses NMP polypeptide with epitopes reactive with the monoclonal antibodies of the invention.

When used for immunotherapy, the monoclonal antibodies of the invention may be unlabeled or attached to a therapeutic agent. These agents can be coupled either directly or indirectly to the monoclonal antibodies of the invention. One example of indirect coupling is by use of a spacer moiety. These spacer moieties, in turn, can be either insoluble or soluble, see Diener et al., *Science* 231: 148 (1986), and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

Non-proteinaceous as well as proteinaceous drugs can be conjugated to the monoclonal antibodies of the present invention. Preferred drugs for conjugation include mitomycin C, daunorubicin, vinblastine, and others used to treat cancer.

The proteinaceous drugs with which the monoclonal antibodies of the invention can be joined include immunomodulators and other biological response modifiers. The term "biological response modifiers" encompasses substances which are involved in modifying the immune response in such manner as to enhance the destruction of an NMP-associated tumor for which the monoclonal antibodies of the invention are specific. Examples of immune response modifiers include such compounds as lymphokines. Lymphokines include tumor necrosis factor, the interleukins, lymphotoxin, macrophage activating factor, migration inhibition factor, colony stimulating factor, and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy certain isotopes may be more preferable than others depending on such factors as tumor cell distribution as well as isotope stability and emission. If desired, the tumor cell distribution can be evaluated by the in vivo diagnostic techniques described above. Depending on the cell proliferative disease some emitters may be preferable to others. In general, alpha and beta particle-emitting radioisotopes are preferred in immunotherapy. For example, if an animal has solid tumor foci a high energy beta emitter capable of penetrating several millimeters of tissue, such as $^{90}$Y, may be preferable. On the other hand, if the cell proliferative disorder consists of simple target cells, as in the case of leukemia, a short range, high energy alpha emitter, such as $^{212}$Bi, may be preferable. Examples of radio-isotopes which can be bound to the monoclonal antibodies of the invention for therapeutic purposes are $^{125}$I, $^{131}$I $^{90}$Y, $^{67}$Cu, $^{212}$Bi, $^{211}$At , $^{212}$Pb , $^{47}$SC, $^{109}$Pd, $^{65}$Zn, and $^{188}$Re.

Lectins are proteins, usually isolated from plant material, which bind to specific sugar moieties. Many lectins are also able to agglutinate cells and stimulate lymphocytes. Ricin is a toxic lectin which has been used immunotherapeutically. The alpha-peptide chain of ricin, which is responsible for toxicity, may be bound to the antibody of the invention to enable site specific delivery of the toxic effect.

Toxins are poisonous substances produced by plants, animals, or microorganisms, that, in sufficient dose, are often lethal. Diphtheria toxin is a substance produced by *Corynebacterium diphtheria* which can be used therapeutically. This toxin consists of an alpha and beta subunit which under proper conditions can be separated. The toxic A component can be bound to an antibody and used for site specific delivery to a NMP bearing cell.

The monoclonal antibodies of the invention can be used in combination with alpha-interferon. This treatment modality enhances monoclonal antibody targeting of carcinomas by increasing the expression of monoclonal antibody reactive antigen by the carcinoma cells. Greiner et al., *Science* 235: 895 (1987). Alternatively, the monoclonal antibody of the invention can be used, for example, in combination with gamma-interferon to thereby activate and increase the expression of Fc receptors by effector cells which, in turn, results in an enhanced binding of the monoclonal antibody to the effector cell and killing of target tumor cells.

It is also possible to utilize liposomes with the monoclonal antibodies of the invention in their membrane to specifically deliver the liposome to the tumor expressing NMP. These liposomes can be produced such that they contain, in addition to the monoclonal antibody, such immunotherapeutic agents as those described above which would then be released at the tumor site. Wolff et al., *Biochem. Biophys.* Acta 802: 259 (1984).

The dosage ranges for the administration of monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

The present invention also provides a method for treating a subject with an NMP-associated cell-proliferative disorder using an NMP nucleotide sequence. An NMP nucleotide sequence which may encode a suppressor polypeptide may be under-expressed as compared to expression in a normal cell, therefore it is possible to design appropriate therapeutic or diagnostic techniques directed to this sequence. Thus, where a cell-proliferative disorder is associated with the expression of an NMP associated with malignancy, nucleic acid sequences that interfere with NMP expression at the translational level can be used. This approach utilizes, for example, antisense nucleic acid and ribozymes to block translation of a specific NMP mRNA, either by masking that mRNA with an antisense nucleic acid or by cleaving it with a ribozyme. In cases when a cell proliferative disorder or abnormal cell phenotype is associated with the under expression of NMP suppressor for example, nucleic acid sequences encoding NMP (sense) could be administered to the subject with the disorder.

Antisense nucleic acids are DNA or RNA molecules that are complementary to at least a portion of a specific mRNA molecule. Weintaub, *Scientific American,* 262: 40 (1990). In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to be expressed than larger molecules when introduced into the target NMP-producing cell.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it. Cech, *J. Amer. Med. Assn.* 260: 3030 (1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative disorders which are mediated by NMP. Such therapy requires introduction of the appropriate NMP polynucleotide sequence (antisense or encoding strand) into cells of subjects having the proliferative disorder. Delivery of antisense NMP polynucleotides can be achieved using a recombinant expression vector such as a chimeric virus or a liposome. Disorders associated with under-expression of an NMP or expression of a cancer-associated NMP can be treated using gene therapy with the encoding or antisense nucleotide sequences, respectively.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting an NMP sequence of interest into the viral vector along with another gene which encodes the ligand for a receptor on a specific target cell, for example, the vector is rendered target specific. Retroviral vectors can be made target specific by inserting, for example, a polynucleotide encoding a sugar, a glycolipid, or a protein. Preferred targeting is accomplished by using an antibody to target the retroviral vector.

Since recombinant retroviruses are defective in one or more genes, they require assistance in order to produce infectious vector particles. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env by conventional calcium phosphate transfection. These cells are then transfected with the vector plasmid containing the genes of interest. The resulting cells release the retroviral vector into the culture medium.

Other targeted delivery systems for NMP antisense polynucleotides include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (ULV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form. Fraley et al., *Trends Biochem. Sci.* 6: 77 (1981).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidyiserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a hyposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies of the invention are preferred receptors. Antibodies can be used to target liposomes to specific cell-surface ligands, in this case the NMPs of choice. Preferably, the target tissue is renal tissue. A number of procedures can be used to covalently attach either polyclonal or monoclonal antibodies to a liposome bilayer. Antibody-targeted liposomes can include monoclonal or polygonal antibodies or fragments thereof such as Fab, or F(ab')$_2$, as long as they bind efficiently to an the antigenic epitope on the target cells.

Preparations for parenteral administration include sterile aqueous or nonaqueous solutions, suspensions, and emulsions. Examples of non aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such an those based on Ringer's dextrose), and the like. Preservatives and other additives may also be present such as, for example, antimicrobials, anti-oxidants, chelating agents and inert gases and the like.

The invention also relates to a method for preparing a medicament or pharmaceutical composition comprising the polynucleotides or the monoclonal antibodies of the invention, the medicament being used for therapy of NMP associated cell proliferative disorders.

The invention is further illustrated by the following, non-limiting examples.

Tissue Samples and Cell Lines

Human tissue samples were obtained from patients undergoing radical nephrectomy for previously diagnosed renal cell cancer at the University of Pittsburgh Medical Center. Matched tumor and normal kidney tissue was obtained from 17 patients. Samples were taken after determination of tumor and normal kidney by gross examination and confirmed by histologic examination of tissue adjacent to the sampled areas. The tissue samples were placed in PBS with 1 mM phenylmethylsulfonyl fluoride (PMSF) and stored at −70° C. until such time that they were processed to extract the nuclear matrix proteins. Tumors were staged according to the TNM system and nuclear grades were assigned according to the Fuhrman system. Tumor stages and grades of the 17 tumors are shown in Table 1.

TABLE 1

Pathologic stage and grade of the tumors studied

| Patient No. | Tumor Type | TNM stage and grade |
| --- | --- | --- |
| 1 | Clear cell and papillary | T2NxMx; II/IV |
| 2 | Clear cell | T3bN1Mx; III/IV |
| 3 | Clear cell | T2NoMx; I/IV |
| 4 | Granular | T3bNoMx; II/IV |
| 5 | Clear cell and granular | T1NxMx; II/IV |
| 6 | Clear cell | T3aNxMx; II/IV |
| 7 | Clear cell and sarcomatoid | T3bNxMx; II and III/IV |
| 8 | Clear | T2NoMx; II/IV |

TABLE 1-continued

Pathologic stage and grade of the tumors studied

| Patient No. | Tumor Type | TNM stage and grade |
| --- | --- | --- |
| 9 | Granular and clear cell | T2NxMx; II/IV |
| 10 | Clear cell | T2NxMx; I/IV |
| 11 | Clear cell | T3bNxMx; II/IV |
| 12 | Clear cell (areas of chromophobe adenoma) | T2NoMx; II/Iv |
| 13 | Clear cell | T2NxMx; II/IV |
| 14 | Poorly differentiated | T4N2M1; IV/IV |
| 15 | Clear cell and granular | T2NxMx; II/IV |
| 16 | Clear cell | T4N1M1; III/IV |
| 17 | Clear cell | T3NxMx; II/IV |

Two cell lines A498 and 769-P obtained from ATCC (Manassas, Va.) were also used for this study. Both cell lines had been established from primary renal cell carcinomas, 769-P from the clear cell type and A498 from papillary RCC. The 769-P cells were grown in RPMI 1640™ medium (GIBCO BRL, Life Technologies, Grand Island, N.Y.) supplemented with L-glutamine, 10% fetal bovine serum, HEPES, sodium pyruvate and 1% penicillin-streptomycin. The A-498 cells were cultivated in modified EAGLES™ medium (GIBCO BRL, Life Technologies, Grand Island, N.Y.) with Earle's basic salt solution and non-essential amino acids supplemented with 10% fetal bovine serum, sodium pyruvate and 1% penicillin-streptomycin.

Nuclear Matrix Preparation

The nuclear matrix proteins (NMPs) were extracted from the tissues and cell lines according to the following method. First, cytoskeletal and nuclear membrane components were removed by salt extraction and treatment with ammonium sulfate. The nuclear chromatin was then removed by using DNase I and RNase, leaving behind the nuclear matrix components.

The pieces of tissue were minced into small (<1 mm$^3$) pieces and homogenized with a Teflon pestle on ice with 0.5% Triton X-100 in a solution containing 2 mM vanadyl ribonucleoside (Rnase inhibitor) to release the lipids and soluble proteins. The homogenized tissue was then filtered through a 350 μm nylon mesh and treated with 0.25M ammonium sulfate to remove the soluble cytoskeletal components. Dnase and Rnase treatment was then used to remove the chromatin. The remaining fraction contained intermediate filaments and NMPs. This was then disassembled with 8M urea and the insoluble components consisting of carbohydrates and extracellular matrix were pelleted out. After dialyzing the urea out, the intermediate filaments were allowed to reassemble and were subsequently removed by centrifugation. The NMPs were precipitated in ethanol. Freshly prepared PMSF was added to all solutions to prevent digestion by serine proteases, 0.3 μM aprotonin, 1 μM leupeptin and 1 μM pepstatin. The protein concentration was determined by resuspending the proteins in PBS or sample buffer and using the Coomassie Plus protein assay using bovine serum albumin as a standard. For electrophoresis, the NMPs which were precipitated in ethanol were dissolved in a sample buffer consisting of 9M urea, 65 mM 3-[(3-cholamidopropyl) -dimethyl-ammonio]-1-propanesulfonate, 2.2% ampholytes and 140 mM DTT (ESA Inc., Chelmsford, Mass.). The final pellet containing the NMPs represented <1% of the total cellular proteins.

High Resolution Two-Dimensional Electrophoresis

Electrophoresis was performed using the INVESTIGATOR 2-D™ gel system (ESA Inc., Chelmsford, Mass.). One-dimensional isoelectric focusing was carried out for 18,000 volt-hours using 1 mm×18 cm tube gels after 1.5 hours of prefocusing. The tube gels were extruded and placed on top of 1 mm SDS DURACRYL™ (ESA Inc., Chelmsford, Mass.) high tensile strength PAGE slab gels. The gels were electrophoresed at 12° C. constant temperature for 4.5 to 5 hours. Gels were fixed with 50% methanol and 10% acetic acid. After thorough rinsing and rehydration, gels were treated with 5% glutaraldehyde and 5 mM DTT after buffering with 50 mM phosphate (pH 7.2). The gels were stained with silver stain (Accurate Chemical Co., Westbury, N.Y.). Fifty μg of protein were loaded per gel. Protein molecular weight standards were silver standards from Diversified Technology (Newton Center, Mass.). Isoelectric points were determined using carbamylated standards (BDH-distributed by Gallard-Schlesinger, Carle Place, NY and Sigma Chemical Co., St. Louis, Mo.). Multiple gels were run for each sample and multiple samples were run at different times. Only protein spots clearly and reproducibly observed in all the gels of a sample type were taken into account as those representing NMPs. The gels were analyzed using the 2D ELECTROPHORESIS ANALYSIS SYSTEM™ (BioImage, Ann Arbor, Mich.) which matches protein spots between gels and sorts the gels and protein spots into a database.

Consistent differences in NMP composition were noted between normal kidney tissue and renal cancer cells in all the samples. Five characteristic and unique NMPs were detected by two-dimensional electrophoresis in all seventeen tumor samples which were absent in the samples of normal kidney tissue (RCCA 1–5). These NMPs were found in all the tumors irrespective of histologic subtype or nuclear grade. In order to limit the possibility that the differences in NMP composition noted in these studies were due to differences in mitotic rates, tumors of various nuclear grades were selected, including nuclear grade II tumors which do not have increased number of mitoses over normal control tissue. One NMP was detected exclusively in all the normal kidney samples and was absent in all the tumor tissues (RCNL-1). All the proteins isolated appear to be unique and their PIs and molecular weights are completely different from those proteins detected in earlier studies in prostate, breast and bladder cancers.

In order to rule out the possibility that the differences in NMP composition may be due to the detection of NMPs from stromal and other cell types admixed with the homogenized sample, the NMP composition of two renal cancer cell lines was also examined. All five of the NMPs identified in the human tumor samples (RCCA 1–5) were also found in both the cell lines.

The following NMPs were identified:

TABLE 2

| Molecular Weight (Daltons) | pI |
| --- | --- |
| Proteins Associated With Human Renal Cancer | |
| RCCA-1    53,000 | 9.30 |
| RCCA-2    32,000 | 6.95 |
| RCCA-3    27,000 | 6.50 |
| RCCA-4    20,000 | 5.25 |
| RCCA-5    15,000 | 6.00 |
| Protein Associated with Normal Human Kidney | |
| RCNL-1    103,000 | 8.30 |

While the invention has been described in detail and with reference to specific embodiments thereof, it will be apparent to one skilled in the art that various changes and modifications can be made therein without departing from the spirit and scope of the invention.

What is claimed is:

1. A purified nuclear matrix protein (NMP), wherein said NMP is selected from the group consisting of:
   (a) RCCA-1 having a molecular weight of about 53 kD and a pI of about 9.30,
   (b) RCCA-2 having a molecular weight of about 32 kD and a pI of about 6.95,
   (c) RCCA-3 having a molecular weight of about 27 kD and a pI of about 6.50,
   (d) RCCA-4 having a molecular weight of about 20 kD and a pI of about 5.25,
   (e) RCCA-5 having a molecular weight of about 15 kD and a pI of about 6.00, and
   (f) RCNL-1 having a molecular weight of about 103 kD and a pI of about 8.30.

2. A method for detecting a cell proliferative disorder in a subject, comprising contacting a cellular component from the subject with a reagent which binds to a cellular component associated with a nuclear matrix protein of claim 1, wherein the expression of said nuclear matrix protein indicates the presence or absence of said cell proliferative disorder.

3. The method of claim 2, wherein the cellular component is taken from the subject's kidney.

4. The method of claim 3, wherein the cellular component is protein.

5. A method for identifying a composition which blocks or enhances the expression of an NMP of renal cells, which method comprises:
   (a) incubating NMP-containing renal cells with a test composition under conditions that allow the renal cells and test composition to interact, and then
   (b) measuring whether the test composition causes blocking or enhancement of the expression of a nuclear matrix protein of claim 1.

6. The method of claim 5, wherein the effect being measured is blocking of the function of the NMP.

7. The method of claim 5, wherein the effect being measured is enhancement of the function of the NMP.

8. A purified nuclear matrix protein as claimed in claim 1, wherein the nuclear matrix protein is RCCA-1 having a molecular weight of about 53 kD and a pI of about 9.30.

9. A purified nuclear matrix protein as claimed in claim 1, wherein the nuclear matrix protein is RCCA-2 having a molecular weight of about 32 kD and a pI of about 6.95.

10. A purified nuclear matrix protein as claimed in claim 1, wherein the nuclear matrix protein is RCCA-3 having a molecular weight of about 27 kD and a pI of about 6.50.

11. A purified nuclear matrix protein as claimed in claim 1, wherein the nuclear matrix protein is RCCA-4 having a molecular weight of about 20 kD and a pI of about 5.25.

12. A purified nuclear matrix protein as claimed in claim 1, wherein the nuclear matrix protein is RCCA-5 having a molecular weight of about 15 kD and a pI of about 6.00.

13. A purified nuclear matrix protein as claimed in claim 1, wherein the nuclear matrix protein is RCNL-1 having a molecular weight of about 103 kD and a pI of about 8.30.

14. The method of claim 2, wherein the reagent is an antibody that binds to said nuclear matrix protein.

\* \* \* \* \*